United States Patent
Takagi et al.

(10) Patent No.: US 11,160,525 B2
(45) Date of Patent: Nov. 2, 2021

(54) IMAGE PROCESSING APPARATUS AND COMPUTER READABLE STORAGE MEDIUM

(71) Applicant: Konica Minolta, Inc., Tokyo (JP)

(72) Inventors: Tatsuya Takagi, Mitaka (JP); Agus Suharno, Hachioji (JP); Amai Shimizu, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 165 days.

(21) Appl. No.: 16/692,400

(22) Filed: Nov. 22, 2019

(65) Prior Publication Data
US 2020/0163640 A1    May 28, 2020

(30) Foreign Application Priority Data
Nov. 22, 2018    (JP) ............................. JP2018-218799

(51) Int. Cl.
*A61B 6/00* (2006.01)
*G06T 7/00* (2017.01)
*G06T 5/50* (2006.01)
*G06T 5/10* (2006.01)
*G06T 5/00* (2006.01)

(52) U.S. Cl.
CPC .......... *A61B 6/5205* (2013.01); *A61B 6/5258* (2013.01); *A61B 6/542* (2013.01); *G06T 5/002* (2013.01); *G06T 5/10* (2013.01); *G06T 5/50* (2013.01); *G06T 7/0012* (2013.01)

(58) Field of Classification Search
CPC .. G06T 5/002; G06T 5/10; G06T 5/50; G06T 7/0012; G06T 2207/10016; G06T 2207/10116; G06T 2207/20182; G06T 2207/20224; G06T 2207/30061; A61B 6/5205; A61B 6/542; A61B 6/5258; A61B 6/486
See application file for complete search history.

(56) References Cited

U.S. PATENT DOCUMENTS

2016/0125268 A1*  5/2016  Ebiyama ............... G06K 9/4642
                                                    382/218
2020/0143517 A1*  5/2020  Zhou ....................... G06T 5/002

FOREIGN PATENT DOCUMENTS

JP          2007044355 A        2/2007

* cited by examiner

*Primary Examiner* — Michael C Bryant
(74) *Attorney, Agent, or Firm* — Cantor Colburn LLP

(57) ABSTRACT

An image processing apparatus includes a hardware processor that: calculates a representative signal value in a region where no signal value variations attributable to dynamic states of an object are present, in each of a plurality of frame images acquired by consecutively applying radiation onto the object a plurality of times, and extracts high-frequency components of changes over time in the calculated representative signal values; and corrects signal value variations attributable to a fact that an irradiation amount varies each time the radiation is applied, by subtracting the extracted high-frequency components from the plurality of frame images, respectively, or dividing the plurality of frame images by the extracted high-frequency components, respectively.

10 Claims, 6 Drawing Sheets

IMAGE PROCESSING APPARATUS AND COMPUTER READABLE STORAGE MEDIUM

CROSS REFERENCE TO RELATED APPLICATIONS

The present invention claims priority under 35 U.S.C. § 119 to Japanese Patent Application No. 2018-218799 filed on Nov. 22, 2018, the entire contents of which are incorporated herein by reference.

BACKGROUND

Technological Field

The present invention relates to an image processing apparatus and a computer readable storage medium.

Description of the Related Art

Conventionally, a radiographic imaging apparatus has been known that performs radiographing several times per second by consecutively applying pulsed radiation from a radiation source onto an object and acquires a moving image including a plurality of frame images that present dynamic states of the object. With such a radiographic imaging apparatus, problems occur, such as flickering when the moving image is displayed and being unable to perform accurate image analysis, due to a fact that an irradiation amount of radiation varies each time the radiation is applied, as shown in FIG. 7.

For a technique that enhances visibility of a displayed projection X-ray image, for example, JP 2007-044355A describes a technique in which a region of interest including a pixel at a specific point designated by a point designator is extracted from image data, and an X-ray condition for an X-ray generator is controlled based on values of pixels in the extracted region of interest.

However, in the technique according to JP 2007-044355A, it is necessary to control the X-ray generator in order to make an X-ray amount optimum to a part that is truly desired to be observed. In addition, since feedback control is performed based on the image data that is acquired by applying X-rays, a delay occurs in responding. Further, minute variations in irradiation amount cannot be suppressed.

SUMMARY

An object of the present invention is to make it possible to suppress signal value variations attributable to variations in irradiation amount among a plurality of frame images acquired by consecutively applying radiation a plurality of times, without controlling the irradiation amount of radiation, and without suppressing object-induced signal value variations.

To achieve the abovementioned object, an image processing apparatus reflecting an aspect of the present invention includes a hardware processor that: calculates a representative signal value in a region where no signal value variations attributable to dynamic states of an object are present, in each of a plurality of frame images acquired by consecutively applying radiation onto the object a plurality of times, and extracts high-frequency components of changes over time in the calculated representative signal values; and corrects signal value variations attributable to a fact that an irradiation amount varies each time the radiation is applied, by subtracting the extracted high-frequency components from the plurality of frame images, respectively, or dividing the plurality of frame images by the extracted high-frequency components, respectively.

A non-transitory computer readable storage medium reflecting another aspect of the present invention stores a program causing a computer to perform: calculating a representative signal value in a region where no signal value variations attributable to dynamic states of an object are present, in each of a plurality of frame images acquired by consecutively applying radiation onto the object a plurality of times, and extracting high-frequency components of changes over time in the calculated representative signal values; and correcting signal value variations attributable to a fact that an irradiation amount varies each time the radiation is applied, by subtracting the extracted high-frequency components from the plurality of frame images, respectively, or dividing the plurality of frame images by the extracted high-frequency components, respectively.

BRIEF DESCRIPTION OF THE DRAWINGS

The abovementioned object, advantages, and features of the present invention will become more fully understood from the detailed description given hereinbelow and the appended drawings which are given by way of illustration only, and thus are not intended as a definition of the limits of the present invention, and wherein.

DETAILED DESCRIPTION OF EMBODIMENTS

Hereinafter, one or more embodiments of the present invention will be described with reference to the drawings. However, the scope of the invention is not limited to the illustrated examples.

(Configuration of a Radiograph Acquisition System 100)

First, a configuration of a present embodiment will be described.

Figure 1:
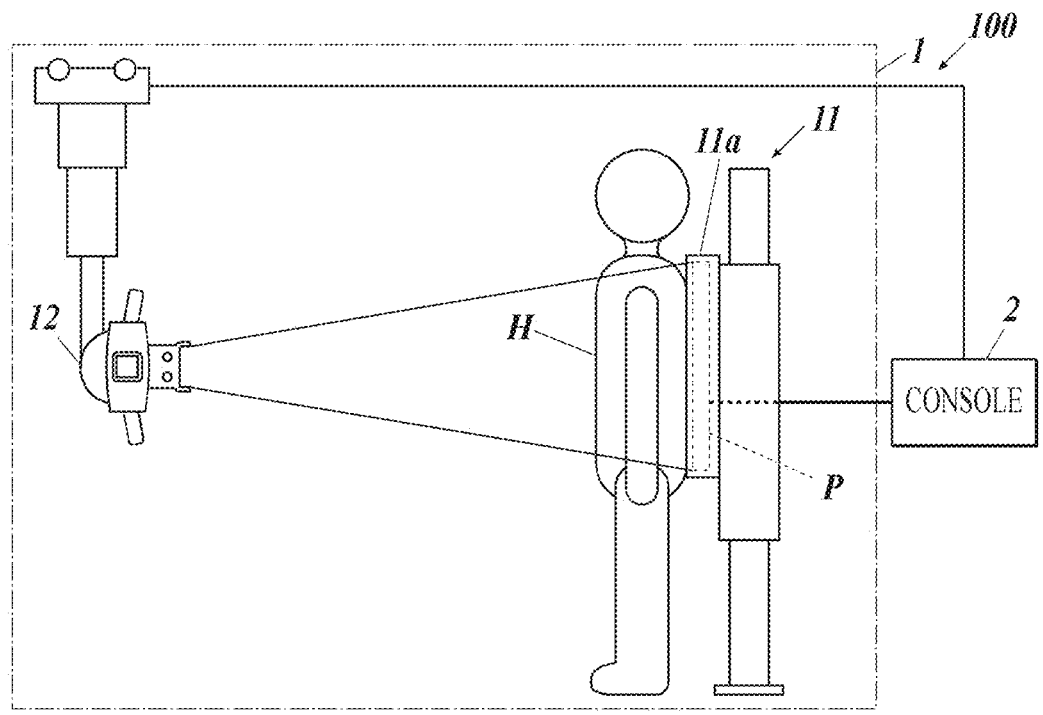
FIG. 1 is a diagram showing an example of an entire configuration of a radiograph acquisition system according to an embodiment of the present invention.

FIG. 1 is a diagram showing an example of an entire configuration of a radiograph acquisition system 100 according to the present embodiment. As shown in FIG. 1, the radiograph acquisition system 100 includes a radiographing apparatus 1 and a console 2, which are connected to each other in such a manner as to be able to transmit and receive data.

For example, the radiographing apparatus 1 is an apparatus that radiographs a moving image of dynamic states of an object H, such as changes in expanding and contracting forms of lungs accompanying respiratory movements and pulsation of a heart. Radiographing a moving image means here acquiring a plurality of images that present the dynamic states of the object H by repeatedly applying pulsed radiation such as X-rays onto the object H at a predetermined time interval. A string of the images acquired by such radiographing is referred to as a moving image. Each of the plurality of images included in the moving image is referred to as a frame image. Note that although description will be given by taking a case of radiographing a moving image of a front side of a chest as an example in the embodiment described below, such an example is not intended as a definition of a limit.

The radiographing apparatus 1 includes a radiation detector P, a radiographing base 11 that can be loaded with the radiation detector P, and a radiation generator 12. The radiographing base 11 is configured in such a manner that a holder 11a on the radiographing base 11 can be loaded with the radiation detector P.

The radiation detector P includes a semiconductor image sensor such as an FPD (Flat Panel Detector), and is installed in such a manner as to face the radiation generator 12 with the object H placed between the radiation detector P and the radiation generator 12. The radiation detector P includes, for example, a glass plate or the like, and a plurality of detection elements (pixels) are arranged in a matrix at predetermined locations on the plate. The pixels detect radiation (X-rays) that is applied from the radiation generator 12 and transmits through at least the object H, according to strength of the radiation, convert the detected radiation into electric signals, and accumulate the electric signals. Each pixel includes a switch such as a TFT (Thin Film Transistor). The radiation detector P controls the switch of each pixel based on an image reading condition inputted from the console 2 to switch reading of the accumulated electric signals from one pixel to another, reads the electric signals accumulated in the individual pixels, and thus acquires image data (signal values). The image data is the frame images. The signal values (pixel values) in each frame image indicate values of density. The radiation detector P outputs the acquired frame images to the console 2.

The radiation generator 12 is disposed at a location facing the radiation detector P with the object H placed between the radiation generator 12 and the radiation detector P, and performs radiographing by applying radiation onto the radiation detector P set in the holder 11a through the object H, based on a radiation application condition inputted from the console 2.

The console 2 controls radiographing and radiograph reading operations of the radiographing apparatus 1 by outputting radiographing conditions such as the radiation application condition and the image reading condition to the radiographing apparatus 1, and also functions as an image processing apparatus that performs image processing of the frame images of the moving image acquired by the radiographing apparatus 1.

Figure 2:
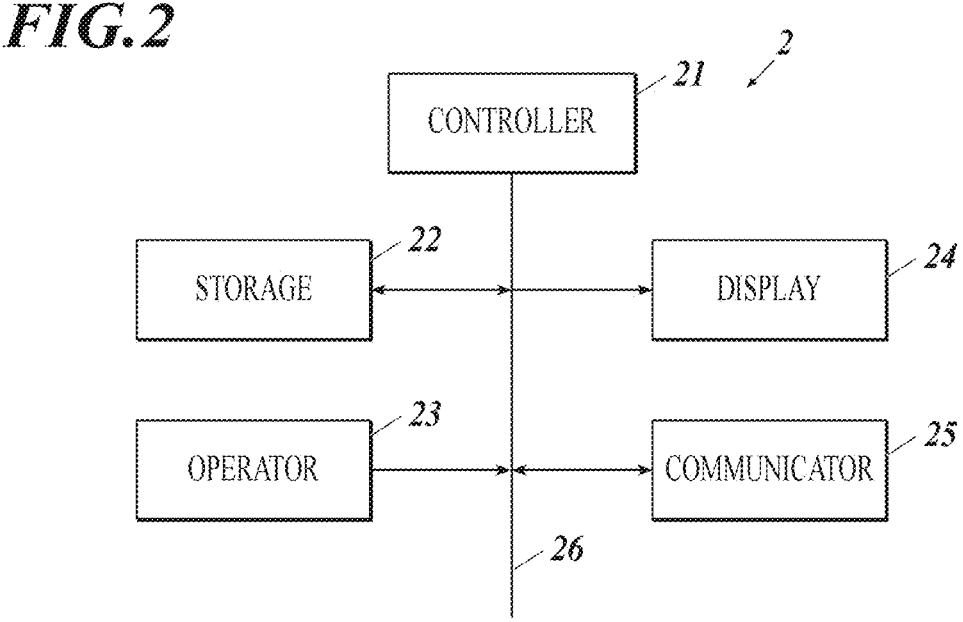
FIG. 2 is a block diagram showing a functional configuration of a console in FIG. 1.

The console 2 includes a controller 21, a storage 22, an operator 23, a display 24, and a communicator 25, which are connected to each other through a bus 26, as shown in FIG. 2.

The controller 21 includes a CPU (Central Processing Unit), a RAM (Random Access Memory), and the like. The CPU of the controller 21 reads a system program and various processing programs stored in the storage 22 and expands the programs in the RAM in accordance with an operation on the operator 23, and controls operations of each unit of the console 2 and a radiation application operation and a reading operation of the radiographing apparatus 1 in a centralized manner in accordance with the expanded programs.

The storage 22 includes a nonvolatile semiconductor memory, a hard disk, or the like. The storage 22 stores the various programs to be executed by the controller 21 and parameters required by the programs for execution of processing, or data such as processing results. The various programs are stored in forms of readable program codes, and the controller 21 sequentially performs operations according to the program codes.

The storage 22 further stores the radiographic conditions (the radiation application condition and the image reading condition) corresponding to a part to be radiographed (here, a chest). The storage 22 still further stores radiographing order information transmitted from an unshown RIS (Radiology Information System) or the like. The radiographing order information includes patient information, examination information (such as an examination ID, a part to be radiographed (including a radiographing direction), and a date of examination), and the like.

The storage 22 stores the moving image acquired by radiographing in association with the patient information and the examination information.

The operator 23 includes a keyboard including cursor keys, numeric keys, various function keys, and the like, and a pointing device such as a mouse, and outputs an instruction signal inputted through a key operation on the keyboard or a mouse operation made by a user to the controller 21. The operator 23 may also include a touch panel on a display screen of the display 24, in which case the operator 23 outputs an instruction signal inputted via the touch panel to the controller 21. Further, the operator 23 includes an exposure switch for instructing the radiation generator 12 to radiograph a moving image.

The display 24 includes a monitor such as an LCD (Liquid Crystal Display) or a CRT (Cathode Ray Tube) and displays an instruction inputted from the operator 23, data, and the like in accordance with an instruction of a display signal inputted by the controller 21.

The communicator 25 includes an interface for transmitting and receiving data to/from the radiation generator 12 and the radiation detector P. Note that communication between the console 2 and each of the radiation generator 12 and the radiation detector P may be wired communication, or may be wireless communication.

Moreover, the communicator 25 includes a LAN adapter, a modem, a TA (Terminal Adapter), and the like and controls data transmission and reception to/from the unshown RIS or the like connected to a communication network.

(Operation of the Radiograph Acquisition System 100)

While the radiographing apparatus 1 is in a state where the radiation detector P is set in the holder 11a, at the console 2, when radiographing order information on a subject of radiographing is selected by using the operator 23, radiographing conditions (a radiation application condition and a radiograph reading condition) corresponding to the selected radiographing order information are read from the storage 22. The radiographing conditions are transmitted to the radiographing apparatus 1 and set on the radiographing apparatus 1. When the object H is positioned and the exposure switch is pressed, then at the radiographing apparatus 1, radiation is consecutively applied a plurality of times by the radiation generator 12, and a plurality of frame images of a moving image are acquired by the radiation detector P, assigned frame numbers, and transmitted to the console 2.

At the console 2, when the moving image from the radiation detector P is received by the communicator 25, the controller 21 stores the received moving image in the storage 22 in association with patient information and examination information. The controller 21 corrects signal value variations attributable to a fact that an irradiation amount varies each time radiation is applied in radiographing, by performing irradiation amount variation correction processing on the received moving image.

Figure 3:
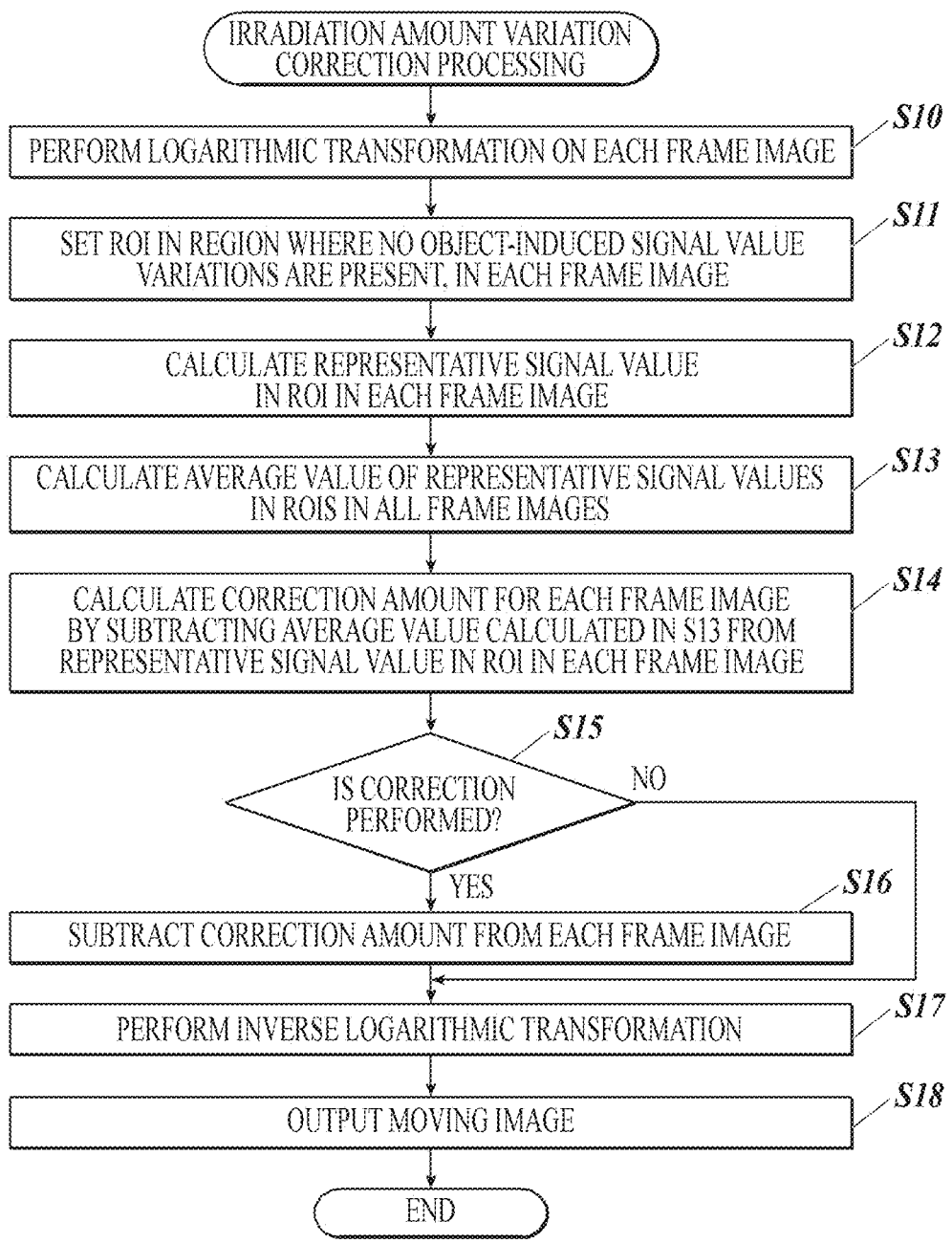
FIG. 3 is a flowchart showing a flow of irradiation amount variation correction processing performed by a controller in FIG. 1.

FIG. 3 is a flowchart showing a flow of the irradiation amount variation correction processing. The irradiation amount variation correction processing is performed through cooperation between the controller 21 and a program stored in the storage 22.

First, the controller 21 performs logarithmic transformation on each frame image (Step S10).

Here, amplitudes of variations in irradiation amount can be made constant by performing the logarithmic transformation of signal values in each frame image.

Next, the controller 21 sets a ROI (region of interest) in a region where no object-induced signal value variations are present (signal value variations attributable to the dynamic states of the object H) in each frame image (Step S11).

Examples of the region where no object-induced signal value variations are present include a region where the radiation directly enters the radiation detector P without transmitting through the object H (a direct radiation region). Moreover, ROIs can also be set in a thoracic vertebra region and a shoulder region, where no signal value variations attributable to respiration movements or heart beat movements are present, as regions where no object-induced signal value variations are present.

A ROI may be automatically set by the controller 21. Alternatively, a frame image of the moving image is displayed on the display 24, and a region designated in the displayed image by a user using the operator 23 may be set as a ROI.

For a method of automatically setting a ROI, for example, the controller 21 analyzes the moving image and identifies a region where no object-induced signal value variations are present, and a ROI is set in the identified region.

Figure 4:
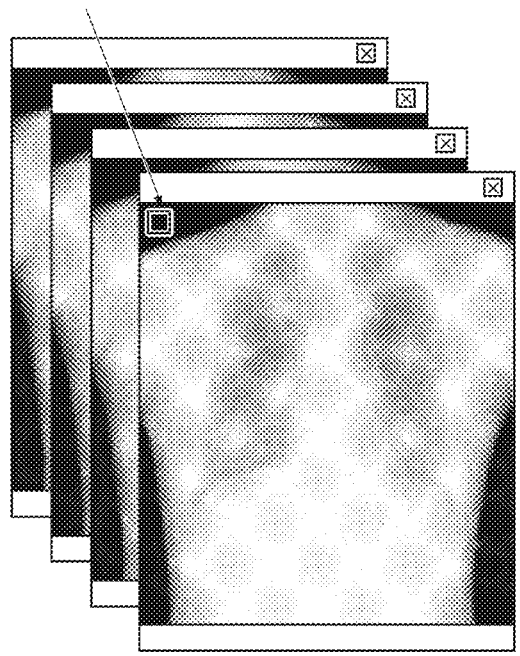
FIG. 4 is a diagram for describing a direct radiation region.
Figure 5:
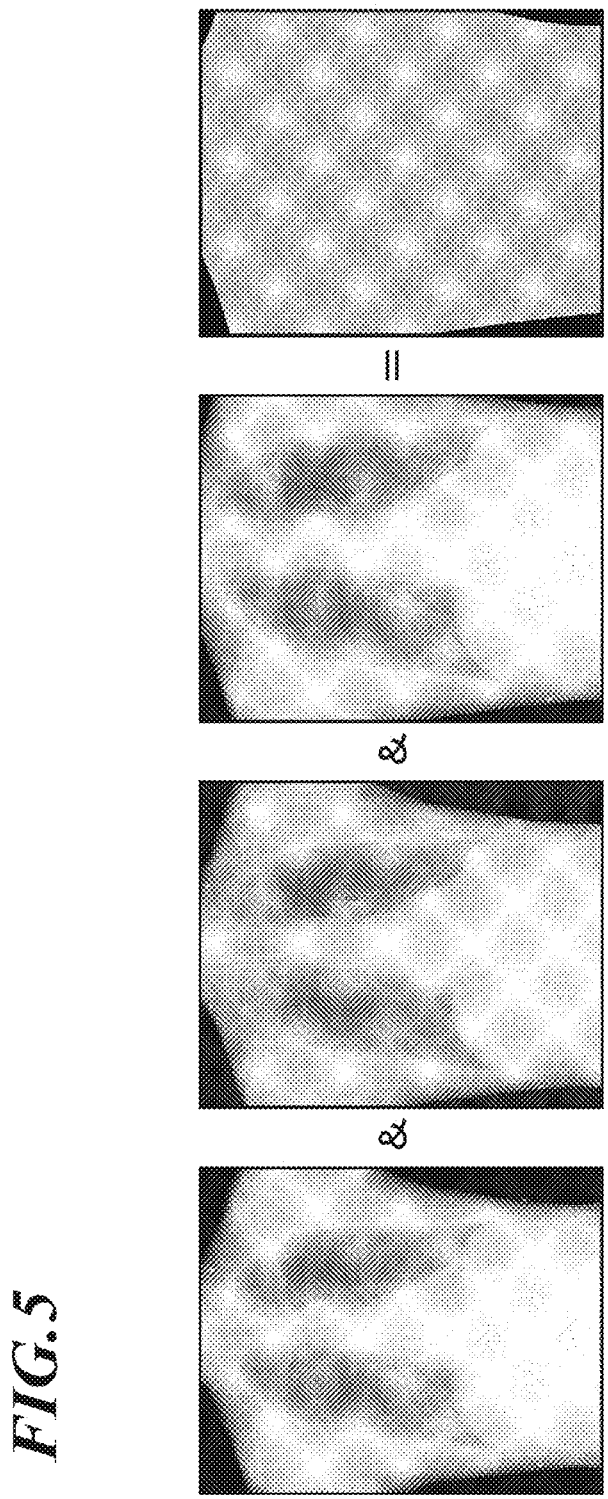
FIG. 5 is a diagram for describing an example of a method of identifying a region where no object-induced signal value variations are present.

For example, a direct radiation region is recognized from the moving image, and a ROI is set within the recognized direct radiation region. A direct radiation region can be recognized by using a known scheme. For example, since signal values in a direct radiation region are much higher than signal values in other regions as shown in FIG. 4, a region in which signal values are not lower than a predetermined threshold value TH1 is recognized as a direct radiation region in each frame image. Then, as shown in FIG. 5, of the direct radiation regions recognized in the individual frame images, a region common to all of the frame images is set as a ROI.

Figure 6:
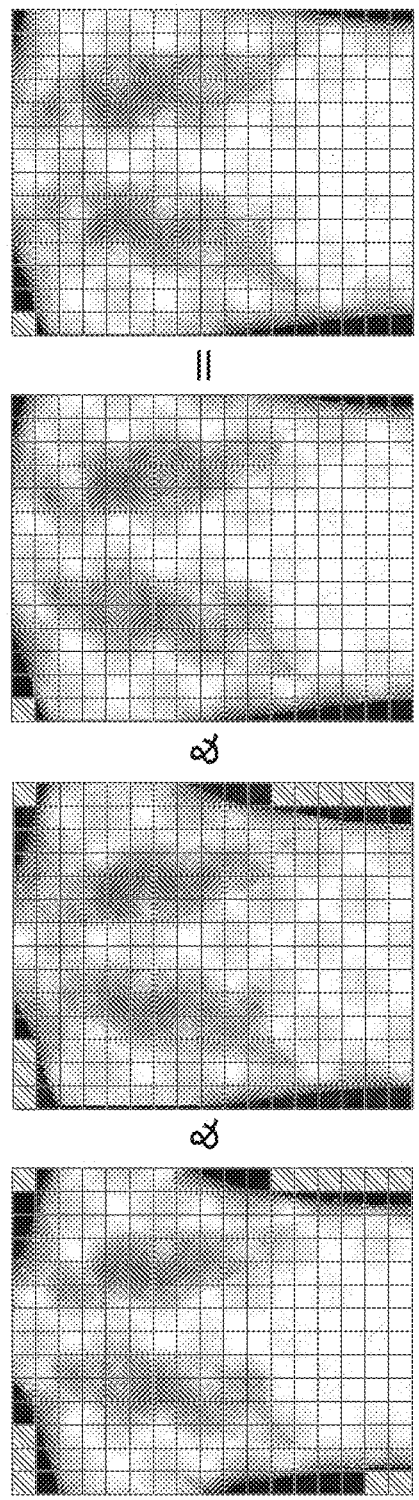
FIG. 6 is a diagram for describing another example of the method of identifying a region where no object-induced signal value variations are present.

Alternatively, as described in JP 05-007579A, since signal values in a direct radiation region are much higher than signal values in other regions and uniform, small regions, each including a plurality of pixels, are set in each frame image, and a group of small regions where, for example, an average signal value in each small region is not lower than a predetermined threshold value TH1 and a variance value in each small region is lower than a predetermined threshold value TH2 is recognized as a direct radiation region. Then, as shown in FIG. 6, of the small regions set within the regions recognized as the direct radiation regions (indicated by hatching in FIG. 6) in the individual frame images, a small region existing in common among all of the frame images is set as a ROI.

Alternatively, a thoracic vertebra region is recognized from the moving image, and a ROI may be set within the recognized thoracic vertebra region. A thoracic vertebra region can be recognized by using a known scheme. For example, as described in JP 2000-79110A, first, right and left ends of thoracic vertebrae are recognized by using a fact that a horizontal profile of signal values of a trachea part (vicinity of upper ends of lung fields) has a shape in which a maximum value is sandwiched between two minimum values. Subsequently, the upper ends of the lung fields are recognized by using a fact that a vertical profile of signal values has a minimum value at vicinity of an upper end of a lung field region. Subsequently, regarding the upper ends of the lung fields as an upper end of the thoracic vertebrae, a location at a predetermined distance from the upper end of the thoracic vertebrae is set as a lower end of the thoracic vertebrae. Then, inflection points in the horizontal profile from the upper end of the thoracic vertebrae to the lower end of the thoracic vertebrae are re-recognized as right and left ends of the thoracic vertebrae, the thoracic vertebra region is thus recognized, and the thoracic vertebra region recognized in each frame image is set as a ROI. Alternatively, based on shapes or the like of the right and left ends of the thoracic vertebras in the recognized thoracic vertebra region, regions of the first to twelfth thoracic vertebrae are recognized from the thoracic vertebra region, the recognized first to twelfth thoracic vertebrae are set as small regions, and of the small regions, a region existing in common among all of the frame images is set as a ROI.

Alternatively, a shoulder region is recognized from the moving image, and a ROI may be set within the recognized shoulder region. A shoulder region can be recognized by using a known scheme. For example, as described in JP 2000-79110A, a shoulder region can be recognized by using a horizontal profile and a vertical profile of signal values.

For another method of automatically setting a ROI, a ROI may be set at a predetermined fixed location (for example, upper left n×m pixels (n and m are natural numbers), or the like) in each frame image.

Note that the controller 21 may display a frame image (for example, a leading frame image) in which the set ROI is marked by a marker on the display 24. A configuration may also be made such that a user can finely adjust a location and a size of the ROI by operating the operator 23.

In the processing of identifying a region where no object-induced signal value variations are present through image analysis, if the controller 21 fails in detecting a region where no object-induced signal value variations are present, the controller 21 may set a ROI at a predetermined fixed location, or may display a notice on the display 24.

Next, the controller 21 calculates a representative value of signal values (referred to as a representative signal value) in the ROI in each frame image (Step S12). For the representative signal value, for example, a median value, an average value, an N-th percentile (N is a positive integer (for example, N=90)) of a cumulative histogram, or the like can be used.

Next, the controller 21 calculates an average value of the representative signal values in the ROIs in all of the frame images (Step S13), and calculates a correction amount for the signal values in each frame image by subtracting the average value calculated in Step S13 from the representative signal value in the ROI in each frame image (Step S14).

Figure 7:
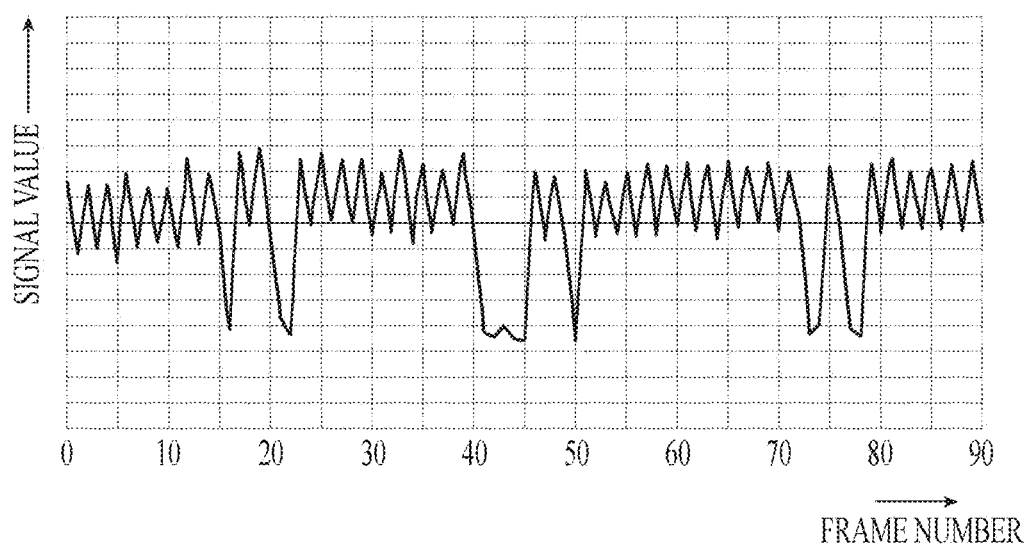
FIG. 7 is a graph showing signal value variations in a time direction attributable to variations in irradiation amount in a moving image.

FIG. 7 is a graph showing changes over time (variations) in signal values of a moving image attributable to variations in irradiation amount during radiographing of a moving image. In radiographing of a moving image, since the irradiation amount varies each time radiation is applied, signal values (signal values representing same places) in a plurality of frame images vary at high frequencies in a time direction, attributable to the variations in irradiation amount. Since no object-induced signal value variations are present in the ROIs set in Step S11, if the representative signal values are plotted in a time series, a profile having high-frequency changes over time similar to the graph shown in FIG. 7 can be obtained. Accordingly, the average value of the representative signal values in the ROIs in all of the frame images is subtracted from the representative signal value in the ROI in each frame image. Thus, a high-frequency component corresponding to the signal value variations attributable to the variations in irradiation amount can be extracted. The high-frequency component is used as a correction amount and subtracted from a signal value of each pixel, whereby irradiation amount-induced variation components can be eliminated from each frame image.

Note that variation components of signal values attributable to variations in irradiation amount may be obtained by extracting a high-frequency component through filtering processing in which a time-direction high-pass filter with a predetermined cutoff frequency is applied to the representative signal value in a ROI.

Next, the controller 21 determines whether or not to perform correction, based on a largest value among absolute values of the calculated correction amounts (Step S15).

Here, if a calculated correction amount is very small or very large, there is a possibility that ROI setting fails because of, for example, failure in automatic recognition of a direct radiation region, thoracic vertebrae, or the like, setting of a ROI in a wrong region by a user, or the like. In such a case, if correction is performed based on the calculated correction amount, there is a possibility that even object-induced signal value variations are eliminated, or the signal value variations attributable to the variations in irradiation amount cannot be eliminated sufficiently even if correction is performed. Accordingly, the controller 21 determines whether or not the largest value of the correction amounts calculated in Step S14 is within a predetermined range and, if the largest value is not within the predetermined range, does not perform correction. Note that it is preferable that the controller 21 notify whether or not correction is performed and locations of the ROIs to a user by, for example, displaying on the display 24 or the like.

If the controller 21 determines to perform correction (Step S15; YES) the controller 21 subtracts the correction amount from the signal value of each pixel in each frame image (Step S16) and then moves to Step S17.

If the controller 21 determines not to perform correction (Step S15; NO), the controller 21 moves to Step S17.

In Step S17, the controller 21 performs inverse logarithmic transformation of the signal values in each frame image (Step S17), outputs a string of the frame images (moving image) subjected to the inverse logarithmic transformation (Step S18), and terminates the irradiation amount variation correction processing.

For example, the controller 21 stores the moving image outputted through the irradiation amount variation correction processing in the storage 22 in association with patient information, examination information, the moving image before correction, and the like, and also displays the moving image on the display 24.

Alternatively, the controller 21 may perform analysis processing on the moving image outputted through the irradiation amount variation correction processing and display a result of the analysis on the display 24. Examples of the analysis processing, which is not particularly limited, include processing of analyzing a ventilation function and processing of analyzing a blood flow function in a case of the moving image of a chest. For the processing of analyzing a ventilation function, for example, processing in which a difference value between a signal value of each pixel in a lung field region in each frame image of the moving image and a signal value of each pixel in a lung field region in a reference frame image (for example, a frame image of a maximal expiratory position or a maximal inspiratory position) is calculated and each frame image is colored with different colors according to the calculated difference values and displayed, or processing in which the calculated difference values are displayed in a form of a graph, can be recited. For the processing of analyzing a blood flow function, for example, processing in which a difference value between a signal value of each pixel in a lung field region in each frame image of the moving image and a signal value of each pixel in a lung field region in an adjacent frame image is calculated and each frame image is colored with different colors according to the calculated difference values and displayed, or processing in which the calculated difference values are displayed in a form of a graph, can be recited. Since the signal value variations attributable to the variations in irradiation amount are eliminated from the moving image outputted through the irradiation amount variation correction processing, analysis can be performed with high accuracy.

Note that the inverse logarithmic transformation in Step S17 may be omitted, for example, if the moving image after the irradiation amount variation correction processing is only displayed on the display 24.

Note that although variations in irradiation amount can also be detected by using a dosimeter (AEC (Automatic Exposure Control) sensor), correction using the variations in irradiation amount detected by using the dosimeter is complicated because efforts and time are needed in linking data between the dosimeter and the console 2 and in temporally matching results of the detection by the dosimeter with images, and therefore the correction through the above-described irradiation amount variation correction processing has an advantage over the correction using the dosimeter.

As described above, the controller 21 of the console 2 calculates a representative signal value in a region where no object-induced signal value variations are present, in each of a plurality of frame images acquired by consecutively applying radiation onto the object H a plurality of times, extracts high-frequency components of changes over time in the calculated representative signal values, and corrects signal value variations attributable to the fact that the irradiation amount varies each time radiation is applied, by subtracting the extracted high-frequency components from the plurality of frame images, respectively.

Accordingly, the signal value variations attributable to variations in irradiation amount can be suppressed in each frame image of the moving image, without controlling the irradiation amount of radiation, and without suppressing object-induced signal value variations. As a result, flicker occurring due to the variations in irradiation amount when the moving image is displayed can be mitigated. Moreover, analysis of the object-induced signal value variations can be performed with high accuracy.

For example, the controller 21 recognizes the region where no object-induced signal value variations are present by performing image analysis of the plurality of frame images and, based on a result of the recognition, identifies the region where no object-induced signal value variations are present, and thus the region where no object-induced signal value variations are present can be identified easily, without a user spending efforts and time.

For example, the controller 21 recognizes a direct radiation region in each of the plurality of frame images and, of the recognized direct radiation regions, identifies a region recognized in common among the plurality of frame images as the region where no object-induced signal value variations are present, or alternatively recognizes the region where no object-induced signal value variations are present in each of the plurality of frame images and, of small regions set in the recognized regions, identifies a small region existing in common among the plurality of frame images as the region where no object-induced signal value variations are present, and thus correction can be performed with higher accuracy.

For example, if the controller 21 fails in identifying the region where no object-induced signal value variations are present through image analysis, a region at a predetermined fixed location is identified as the region where no object-induced signal value variations are present, and thus correction can be performed even if the controller 21 fails in identifying the region where no object-induced signal value variations are present. Moreover, a notice is outputted when the controller 21 fails in identifying the region where no object-induced signal value variations are present, and thus a user can recognize that identification of the region where no object-induced signal value variations are present fails.

For example, by identifying a region designated by user operation, or a region at a predetermined fixed location, as the region where no object-induced signal value variations are present, the region where no object-induced signal value variations are present can be identified easily without performing image analysis.

Moreover, by determining whether or not to perform correction based on the high-frequency components extracted from the regions where no object-induced signal value variations are present, it is possible to avoid eliminating even object-induced signal value variations by correction, and performing ineffective, useless correction.

Note that the description of the disclosed embodiments is made for a purpose of giving preferred examples of the present invention and is not intended as a definition of limits.

For example, in the disclosed embodiments, it is described that the signal value variations attributable to the variations in irradiation amount during radiographing are corrected by subtracting the correction amount from the signal values in each frame image. However, the signal value variations attributable to the variations in irradiation amount during radiographing may be corrected by dividing the signal values in each frame image by the correction amount.

Moreover, for example, although the above description discloses an example in which a hard disk, a nonvolatile semiconductor memory, or the like is used for a computer readable medium storing the program according to the present invention, the computer readable medium is not limited to such an example. As other computer readable media, portable storage media such as a CD-ROM can be applied. Carrier waves can also be applied as a medium that provides data of the program according to the present invention via a communication link.

In addition, detailed components and detailed operations of each device included in a measurement apparatus can also be changed as appropriate without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. An image processing apparatus comprising
a hardware processor that: calculates a representative signal value in a region where no signal value variations attributable to dynamic states of an object are present, in each of a plurality of frame images acquired by consecutively applying radiation onto the object a plurality of times, and extracts high-frequency components of changes over time in the calculated representative signal values; and corrects signal value variations attributable to a fact that an irradiation amount varies each time the radiation is applied, by subtracting the extracted high-frequency components from the plurality of frame images, respectively, or dividing the plurality of frame images by the extracted high-frequency components, respectively.

2. The image processing apparatus according to claim 1, wherein the hardware processor identifies the region where no signal value variations attributable to the dynamic states of the object are present, in each of the plurality of frame images.

3. The image processing apparatus according to claim 2, wherein the hardware processor recognizes the region where no signal value variations attributable to the dynamic states of the object are present by performing image analysis of the plurality of frame images and, based on a result of the recognition, identifies the region where no signal value variations attributable to the dynamic states of the object are present.

4. The image processing apparatus according to claim 3, wherein the hardware processor recognizes a direct radiation region in each of the plurality of frame images and identifies the recognized direct radiation region as the region where no signal value variations attributable to the dynamic states of the object are present.

5. The image processing apparatus according to claim 4, wherein the hardware processor recognizes the direct radiation region in each of the plurality of frame images and, of the recognized direct radiation regions, identifies a region recognized in common among the plurality of frame images as the region where no signal value variations attributable to the dynamic states of the object are present.

6. The image processing apparatus according to claim 3, wherein the hardware processor recognizes the region where no signal value variations attributable to the dynamic states of the object are present in each of the plurality of frame images and, of small regions set in the recognized regions, identifies a small region existing in common among the plurality of frame images as the region where no signal value variations attributable to the dynamic states of the object are present.

7. The image processing apparatus according to claim 3, wherein if the hardware processor fails in identifying the region where no signal value variations attributable to the dynamic states of the object are present by performing image analysis, the hardware processor identifies a region at a predetermined fixed location as the region where no signal value variations attributable to the dynamic states of the object are present, or outputs a notice.

8. The image processing apparatus according to claim 2, wherein the hardware processor identifies a region designated by user operation, or a region at a predetermined fixed location, as the region where no signal value variations attributable to the dynamic states of the object are present.

9. The image processing apparatus according to claim 1, wherein the hardware processor determines whether or not to perform the correction, based on the extracted high-frequency components.

10. A non-transitory computer readable storage medium storing a program causing a computer to perform:
  calculating a representative signal value in a region where no signal value variations attributable to dynamic states of an object are present, in each of a plurality of frame images acquired by consecutively applying radiation onto the object a plurality of times, and extracting high-frequency components of changes over time in the calculated representative signal values; and
  correcting signal value variations attributable to a fact that an irradiation amount varies each time the radiation is applied, by subtracting the extracted high-frequency components from the plurality of frame images, respectively, or dividing the plurality of frame images by the extracted high-frequency components, respectively.

\* \* \* \* \*